US012718914B2

(12) United States Patent
Lau

(10) Patent No.: US 12,718,914 B2
(45) Date of Patent: Aug. 25, 2026

(54) DATABASE RECORD LINKAGE USING ADAPTIVE DYNAMIC BLOCKING

(71) Applicant: Optum, Inc., Minnetonka, MN (US)

(72) Inventor: Yee Lau, Carol Stream, IL (US)

(73) Assignee: Optum, Inc., Minnetonka, MN (US)

(*) Notice: Subject to any disclaimer, the term of this patent is extended or adjusted under 35 U.S.C. 154(b) by 236 days.

(21) Appl. No.: 18/175,649

(22) Filed: Feb. 28, 2023

(65) Prior Publication Data

US 2024/0290445 A1 Aug. 29, 2024

(51) Int. Cl.
*G16H 10/60* (2018.01)
*G06F 16/28* (2019.01)

(52) U.S. Cl.
CPC .......... *G16H 10/60* (2018.01); *G06F 16/288* (2019.01)

(58) Field of Classification Search
CPC .............................. G16H 10/60; G06F 16/288
See application file for complete search history.

(56) References Cited

U.S. PATENT DOCUMENTS 9,081,817 B2 * 7/2015 Arasu ............... G06F 16/24564
10,467,201 B1 * 11/2019 Merritt .................. G06F 16/215
10,599,614 B1 * 3/2020 Borthwick ............. G06N 5/022
10,628,396 B1 * 4/2020 Borthwick ............ G06F 16/215
2004/0019593 A1 * 1/2004 Borthwick ........ G06F 16/24578
2013/0212103 A1 * 8/2013 Cao ....................... G06F 16/215 707/E17.046
2014/0330845 A1 * 11/2014 Feldschuh ............ G06F 16/215 707/749
2015/0254308 A1 * 9/2015 Scott ....................... G06F 16/23 707/780
2020/0364243 A1 * 11/2020 Tamayo-Rios ...... G06F 16/2458

OTHER PUBLICATIONS

Christen, Peter. "A survey of indexing techniques for scalable record linkage and deduplication." IEEE transactions on knowledge and data engineering 24.9 (2011): 1537-1555. (Year: 2011).*
Baxter, R., P. Christen, and T. Churches. "A Comparison of Fast Blocking Methods for Record Linkage; erschienen in: Proceedings of the Workshop on Data Cleaning, Record Linkage and Object Consolidation at the Ninth ACM SIGKDD International Conference on Knowledge Discovery and Data Mining." 2003 (Year: 2003).*
Bitton, Dina, and David J. DeWitt. "Duplicate record elimination in large data files." ACM Transactions on database systems (TODS) 8.2 (1983): 255-265. (Year: 1983).*

(Continued)

*Primary Examiner* — Mohsen Almani
(74) *Attorney, Agent, or Firm* — MARSHALL, GERSTEIN & BORUN LLP

(57) ABSTRACT

A method includes performing by a host system processor: providing a database including a plurality of records, the database having at least one attribute associated therewith; determining a plurality of maximum block sizes as a plurality of ideal maximum numbers of the plurality of records in a plurality of blocks, respectively, based on a plurality of blocking keys; determining a duplication factor based on a number of unique records of the plurality of records based on all of the at least one attribute; and generating candidate pairs of the plurality of records for linkage based on the plurality of maximum block sizes and the duplication factor.

20 Claims, 7 Drawing Sheets

(56) References Cited

OTHER PUBLICATIONS

Anindya, Imrul Chowdhury. Understanding and mitigating privacy risks raised by record linkage. The University of Texas at Dallas, 2020. (Year: 2020).*

McNeill, N., Hakan Kardes, and Andrew Borthwick. "Dynamic record blocking: efficient linking of massive databases in mapreduce." Proceedings of the 10th international workshop on quality in databases (QDB). 2012. (Year: 2012).*

Zhang, Juemin. Adaptive grid computing. Diss. Northeastern University, 2010. (Year: 2010).*

Borthwick, Andrew, et al. "Scalable blocking for very large databases." ECML PKDD 2020 Workshops: Workshops of the European Conference on Machine Learning and Knowledge Discovery in Databases (ECML PKDD 2020): SoGood 2020, PDFL 2020, MLCS 2020, NFMCP 2020, DINA 2020, EDML 2020, XKDD 2020 and INRA 2020 (Year: 2020).*

* cited by examiner

DATABASE RECORD LINKAGE USING ADAPTIVE DYNAMIC BLOCKING

BACKGROUND

The present disclosure relates to computer systems, and, in particular, to methods, systems, and computer program products for managing information in a computer database.

"Record linkage" is a term used to describe the process of joining records from one data source with other records from another data source that describe the same entity. Records from different datasets may be compared based on one or more pre-selected attributes to determine how similar or different the two records are. Pairs of records that are scored similarly may be deemed a matched pair with record linkage being based on these matched pairs. For large datasets the number of comparisons can be very high. Blocking is a technique of selecting attributes in the datasets for more efficient record pairing to reduce the number of comparisons. Attributes or fields selected for blocking are called blocking attributes or blocking fields. Records that have the same value in their blocking field are grouped together as a block. Records grouped together in the same block may then be compared as candidate pairs for linkage. A poor blocking attribute or field selection can result in a large number of comparisons, which may significantly consume computing and/or memory resources.

SUMMARY

In some embodiments of the inventive concept, a method comprises, performing by a host system processor: providing a database including a plurality of records, the database having at least one attribute associated therewith; determining a plurality of maximum block sizes as a plurality of ideal maximum numbers of the plurality of records in a plurality of blocks, respectively, based on a plurality of blocking keys; determining a duplication factor based on a number of unique records of the plurality of records based on all of the at least one attribute; and generating candidate pairs of the plurality of records for linkage based on the plurality of maximum block sizes and the duplication factor.

In other embodiments, a number of the at least one attribute is N; and the method further comprises: generating the plurality of blocking keys comprising: generating a first one of the plurality of blocking keys by selecting a first one of the at least one attribute as the first one of the plurality of blocking keys; then iteratively generating N−1 additional ones of the plurality of blocking keys by adding an additional one of the at least one attribute to a previously created one of the plurality of blocking keys.

In still other embodiments, determining the duplication factor further comprises: determining the duplication factor as 1−(the number of unique records/a total number of the plurality of records).

In still other embodiments, generating the candidate pairs comprises: when the duplication factor is greater than a threshold, performing operations as follows: generating a duplication blocking key using all of the at least one attribute; for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

In still other embodiments, generating the candidate pairs comprises: when the duplication factor is not greater than a threshold, performing operations as follows: for each unique value of a first one of the plurality of blocking keys in the plurality of records, associating ones of the plurality of records having the unique value into a respective block; for each block of the plurality of records, comparing a number of the plurality of records in the block with the one of the plurality of maximum block sizes corresponding to the first one of the plurality of blocking keys to determine if the number of the plurality of records in the block exceeds the one of the plurality of maximum block sizes corresponding to the first one of the plurality of blocking keys; and for each block of the plurality of records for which the number of the plurality of records in the block does not exceed the one of the plurality of maximum block sizes corresponding to the first one of the plurality of blocking keys, generating the candidate pairs by pairing a first one of the plurality of records in the block with each of other ones of the plurality of records in the block, respectively.

In still other embodiments, generating the candidate pairs further comprises: for each block of the plurality of records for which the number of the plurality of records in the block exceeds the one of the plurality of maximum block sizes corresponding to the first one of the plurality of blocking keys, performing operations as follows: for each unique value of a second one of the plurality of blocking keys in the ones of the plurality of records in the block, associating ones of the plurality of records in the block into a respective sub-block; for each sub-block of the ones of the plurality of records, comparing a number of the ones of the plurality of records in the sub-block with the one of the plurality of maximum block sizes corresponding to the second one of the plurality of blocking keys to determine if the number of the ones of the plurality of records in the sub-block exceeds the one of the plurality of maximum block sizes corresponding to the second one of the plurality of blocking keys; and for each sub-block of the ones of the plurality of records for which the number of the ones of the plurality of records in the sub-block does not exceed the one of the plurality of maximum block sizes corresponding to the second one of the plurality of blocking keys, generating the candidate pairs by pairing a first one of the ones of the plurality of records in the sub-block with each of other ones of the plurality of records in the sub-block, respectively.

In still other embodiments, determining the plurality of maximum block sizes comprises: for each of the plurality of blocking keys performing the following operations: for each unique value of the respective one of the plurality of blocking keys, determining a number of ones of the plurality of records having the unique value, which is given by C1, C2, . . . ; and determining the respective maximum block size M for the respective one of the plurality of blocking keys as follows: M=(Max (C1, C2, . . . )/Average (C1, C2, . . . ))+Average (C1, C2, . . . )+Skewness (C1, C2, . . . ).

In still other embodiments, the plurality of records comprise health care records associated with a patient.

In some embodiments of the inventive concept, a system comprises: a processor; and a memory coupled to the processor and comprising computer readable program code embodied in the memory that is executable by the processor to perform operations comprising: providing a database including a plurality of records, the database having at least one attribute associated therewith; determining a plurality of maximum block sizes as a plurality of ideal maximum numbers of the plurality of records in a plurality of blocks, respectively, based on a plurality of blocking keys; determining a duplication factor based on a number of unique records of the plurality of records based on all of the at least one attribute; and generating candidate pairs of the plurality of records for linkage based on the plurality of maximum block sizes and the duplication factor.

In further embodiments, a number of the at least one attribute is N; and the operations further comprise: generating the plurality of blocking keys comprising: generating a first one of the plurality of blocking keys by selecting a first one of the at least one attribute as the first one of the plurality of blocking keys; then iteratively generating N−1 additional ones of the plurality of blocking keys by adding an additional one of the at least one attribute to a previously created one of the plurality of blocking keys.

In still further embodiments, determining the duplication factor further comprises: determining the duplication factor as 1−(the number of unique records/a total number of the plurality of records).

In still further embodiments, generating the candidate pairs comprises: when the duplication factor is greater than a threshold, performing operations as follows: generating a duplication blocking key using all of the at least one attribute; for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

In still further embodiments, generating the candidate pairs comprises: when the duplication factor is not greater than a threshold, performing operations as follows: for each unique value of a first one of the plurality of blocking keys in the plurality of records, associating ones of the plurality of records having the unique value into a respective block; for each block of the plurality of records, comparing a number of the plurality of records in the block with the one of the plurality of maximum block sizes corresponding to the first one of the plurality of blocking keys to determine if the number of the plurality of records in the block exceeds the one of the plurality of maximum block sizes corresponding to the first one of the plurality of blocking keys; and for each block of the plurality of records for which the number of the plurality of records in the block does not exceed the one of the plurality of maximum block sizes corresponding to the first one of the plurality of blocking keys, generating the candidate pairs by pairing a first one of the plurality of records in the block with each of other ones of the plurality of records in the block, respectively.

In still further embodiments, generating the candidate pairs further comprises: for each block of the plurality of records for which the number of the plurality of records in the block exceeds the one of the plurality of maximum block sizes corresponding to the first one of the plurality of blocking keys, performing operations as follows: for each unique value of a second one of the plurality of blocking keys in the ones of the plurality of records in the block, associating ones of the plurality of records in the block into a respective sub-block; for each sub-block of the ones of the plurality of records, comparing a number of the ones of the plurality of records in the sub-block with the one of the plurality of maximum block sizes corresponding to the second one of the plurality of blocking keys to determine if the number of the ones of the plurality of records in the sub-block exceeds the one of the plurality of maximum block sizes corresponding to the second one of the plurality of blocking keys; and for each sub-block of the ones of the plurality of records for which the number of the ones of the plurality of records in the sub-block does not exceed the one of the plurality of maximum block sizes corresponding to the second one of the plurality of blocking keys, generating the candidate pairs by pairing a first one of the ones of the plurality of records in the sub-block with each of other ones of the plurality of records in the sub-block, respectively.

In still further embodiments, determining the plurality of maximum block sizes comprises: for each of the plurality of blocking keys performing the following operations: for each unique value of the respective one of the plurality of blocking keys, determining a number of ones of the plurality of records having the unique value, which is given by C1, C2, . . . ; determining the respective maximum block size M for the respective one of the plurality of blocking keys as follows: and M=(Max (C1, C2, . . . )/Average (C1, C2, . . . ))+Average (C1, C2, . . . )+Skewness (C1, C2, . . . ).

In still further embodiments, the plurality of records comprise health care records associated with a patient.

In some embodiments, of the inventive concept, a computer program product comprises: a non-transitory computer readable storage medium comprising computer readable program code embodied in the medium that is executable by a processor to perform operations comprising: providing a database including a plurality of records, the database having at least one attribute associated therewith; determining a plurality of maximum block sizes as a plurality of ideal maximum numbers of the plurality of records in a plurality of blocks, respectively, based on a plurality of blocking keys; determining a duplication factor based on a number of unique records of the plurality of records based on all of the at least one attribute; and generating candidate pairs of the plurality of records for linkage based on the plurality of maximum block sizes and the duplication factor.

In other embodiments, the duplication factor further comprises: determining the duplication factor as 1−(the number of unique records/a total number of the plurality of records).

In still other embodiments, generating the candidate pairs comprises: when the duplication factor is greater than a threshold, performing operations as follows: generating a duplication blocking key using all of the at least one attribute; for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

In still other embodiments, generating the candidate pairs comprises: when the duplication factor is not greater than a threshold, performing operations as follows: for each unique value of a first one of the plurality of blocking keys in the plurality of records, associating ones of the plurality of records having the unique value into a respective block; for each block of the plurality of records, comparing a number of the plurality of records in the block with the one of the plurality of maximum block sizes corresponding to the first one of the plurality of blocking keys to determine if the number of the plurality of records in the block exceeds the one of the plurality of maximum block sizes corresponding to the first one of the plurality of blocking keys; and for each block of the plurality of records for which the number of the plurality of records in the block does not exceed the one of the plurality of maximum block sizes corresponding to the first one of the plurality of blocking keys, generating the candidate pairs by pairing a first one of the plurality of records in the block with each of other ones of the plurality of records in the block, respectively.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive concept and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
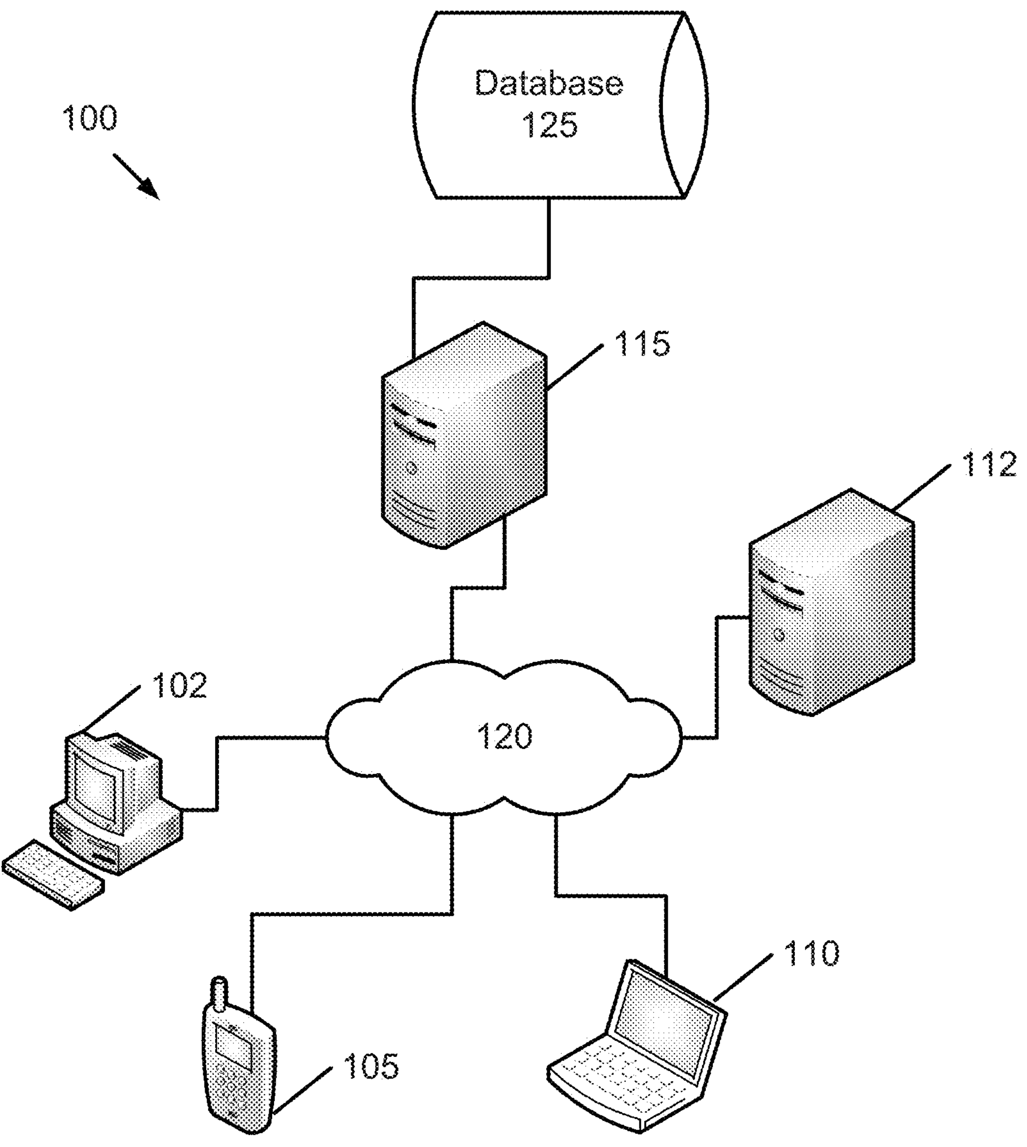
FIG. 1 is a block diagram that illustrates a communication network including various dataset source systems that communicate with a database management system server host for creating a database with multiple datasets according to some embodiments of the inventive concept.

In the following detailed description, numerous specific details are set forth to provide a thorough understanding of embodiments of the present disclosure. However, it will be understood by those skilled in the art that the present invention may be practiced without these specific details. In some instances, well-known methods, procedures, components and circuits have not been described in detail so as not to obscure the present disclosure. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, a "service" includes, but is not limited to, a software and/or hardware service, such as cloud services in which software, platforms, and infrastructure are provided remotely through, for example, the Internet. A service may be provided using Software as a Service (SaaS), Platform as a Service (PaaS), and/or Infrastructure as a Service (IaaS) delivery models. In the SaaS model, customers generally access software residing in the cloud using a thin client, such as a browser, for example. In the PaaS model, the customer typically creates and deploys the software in the cloud sometimes using tools, libraries, and routines provided through the cloud service provider. The cloud service provider may provide the network, servers, storage, and other tools used to host the customer's application(s). In the IaaS model, the cloud service provider provides physical and/or virtual machines along with hypervisor(s). The customer installs operating system images along with application software on the physical and/or virtual infrastructure provided by the cloud service provider.

As used herein, the term "data processing facility" includes, but it is not limited to, a hardware element, firmware component, and/or software component. A data processing system may be configured with one or more data processing facilities.

As used herein, a "field" is the intersection of an "attribute" and a record. This may be illustrated by way of example: A database table may have multiple attributes, such as name, address, phone number, etc. Each record in the table has the data on one entity, such as a customer. The name of a specific customer will be stored in the field that is the intersection of the name attribute and the record for that specific customer.

Embodiments of the inventive concept are described herein in the context of linking records from different data sets in database, such as a relational database. It will be understood that embodiments of the inventive concept are not limited in their application to a relational database model as other database models, such as, but not limited to a flat database model, a hierarchical database model, a network database model, an object-relational database model, and a star schema database model may also be used.

Some embodiments of the inventive concept stem from a realization that the efficiency of linking records in a database in terms of utilization of computing and memory resources relies on the ability to effectively select blocking attributes that result in manageable sized blocks. Some blocking techniques rely on the manual selection of blocking attributes, which may assume that the records in the different datasets have the same fixed natural groupings. For example, blocks may be blocked or grouped based on postal code, date of birth, a unique identifier, etc. However, natural groupings of records may vary during runtime from batch-to-batch. A conventional record linkage process typically involves providing a database with records associated with different datasets, which may have originated from different sources. These records are normalized or pre-processed to ensure that data values for the various fields are expressed in a consistent manner. For example, a person named William J. Smith might appear in different data sets as "William J. Smith," "Smith, W. J.," and "Bill Smith." The records may be updated to ensure a consistent format is used for the same attribute in the fields across all of the records. One or more attributes are selected as blocking attributes and records that have the same field values for those attributes are grouped together in a block. Comparisons are then made between the records in the block to determine similarities between the records and those records that satisfy a similarity may then be linked. The attribute selection for blocking is typically performed manually by a database manager who has domain specific knowledge of the various datasets in the database. This manual process, however, may cause delays and inaccuracies in automating the record linkage process during runtime.

Some embodiments of the inventive concept may provide an adaptive dynamic blocking technique that can be used at run time to generate blocks that can be used for record comparison to identify candidate pairs for linkage. The database may include a plurality of records and may have at least on attribute associated therewith. A plurality of maximum block sizes may be determined based on a plurality of blocking keys. A duplication factor may also be determined to identify databases with large numbers of duplicate records based on all of the database attributes. Candidate pairs for linkage may then be generated based on the maximum block sizes and the duplication factor. By limiting the number of records in a block to a maximum number, the number of comparisons can likewise be limited resulting in a reduction in the amount of computing and memory resources used for the comparison process. Moreover, the blocking, comparing, and linking operations may be implemented on a distributed, parallel computing system cluster. A fixed computing and/or memory resource requirement for the computing system cluster may be inadequate for large block sizes. By dynamically determining the maximum block size for the comparison and linking operations, the resource needs for the computing system cluster may be determine dynamically to adapt to the record volume.

Referring to FIG. 1, a communication network including various dataset source systems that communicate with a database management system server host for creating a database with multiple datasets, in accordance with some embodiments of the inventive concept, comprises client devices 102, 105, and 110 along with an application server 112 that are coupled to a database management system server host 115 via a network 120. The network 120 may be a global network, such as the Internet or other publicly accessible network. Various elements of the network 120 may be interconnected by a wide area network, a local area network, an Intranet, and/or other private network, which may not be accessible by the general public. Thus, the communication network 120 may represent a combination of public and private networks or a virtual private network (VPN). The network 120 may be a wireless network, a wireline network, or may be a combination of both wireless and wireline networks. The client devices 102, 105, 110 may represent wired and/or wireless devices that include one or more applications that use data records that, in some embodiments, may allow a user to interact and perform transactions on the database 125 via the database system server 115. The application server 112 may likewise represent a server, mainframe, enterprise computing system, or other data processing system that may allow one or more users to interact and perform transactions on the database 125. The client devices 102, 105, 110 and the application server 112 that are configured to support an application for performing transactions on the database 125 by way of the database system server host 115 may be the source of one or more datasets for storage in the database 125. For example, client devices 102, 105, 110, and the application server 112 may each be the source of one or more electronic medical records for various patients. A patient, for example, may see multiple health care providers with each provider generating a medical record to document the encounters and care plan for the patient. These providers, however, may desire to review the patient's full medical record, which may include records from multiple sources. Accordingly, it may be desirable to link records associated with the same patient in the database 125 so that the patient's health care service providers may review the patient's medical records across multiple providers. The client devices or terminals 102, 105, 110 and application server 112 may be connected directly to the database management system server host 115 without going through the network 120 in other embodiments of the inventive concept. It will be appreciated that in accordance with various embodiments of the inventive concept, the client devices or terminals 102, 105, 110, application server 112, and database system management server host 115 may be implemented as single processor systems, multi-processor systems, single server systems, separate server systems, or a network of servers either co-located in a server farm, for example, or located in different geographic regions.

As shown in FIG. 1, some embodiments according to the inventive concept can operate in a logically separated client side/server side-computing environment, sometimes referred to hereinafter as a client/server environment. The client/server environment is a computational architecture that involves a client process (i.e., client devices/systems 102, 105, 110, and 112) requesting service from a server process (i.e., database management system server host 115). In general, the client/server environment maintains a distinction between processes, although client and server processes may operate on different machines or on the same machine. Accordingly, the client and server sides of the client/server environment are referred to as being logically separated. Usually, when client and server processes operate on separate devices, each device can be customized for the needs of the respective process. For example, a server process can "run on" a system having large amounts of memory and disk space, whereas the client process often "runs on" a system having a graphic user interface provided by high-end video cards and large-screen displays.

The clients and servers can communicate using a standard communications mode, such as Hypertext Transport Protocol (HTTP), SOAP, XMLL-RPC, and/or WSDL. According to the HTTP request-response communications model, HTTP requests are sent from the client to the server and HTTP responses are sent from the server to the client in response to an HTTP request. In operation, the server waits for a client to open a connection and to request information, such as a Web page. In response, the server sends a copy of the requested information to the client, closes the connection to the client, and waits for the next connection. It will be understood that the server can respond to requests from more than one client.

Although FIG. 1 illustrates an example communication network including various dataset source systems that communicate with a database management system server host for creating a database with multiple datasets, it will be understood that embodiments of the inventive concept are not limited to such configurations, but are intended to encompass any configuration capable of carrying out the operations described herein.

Figure 2:
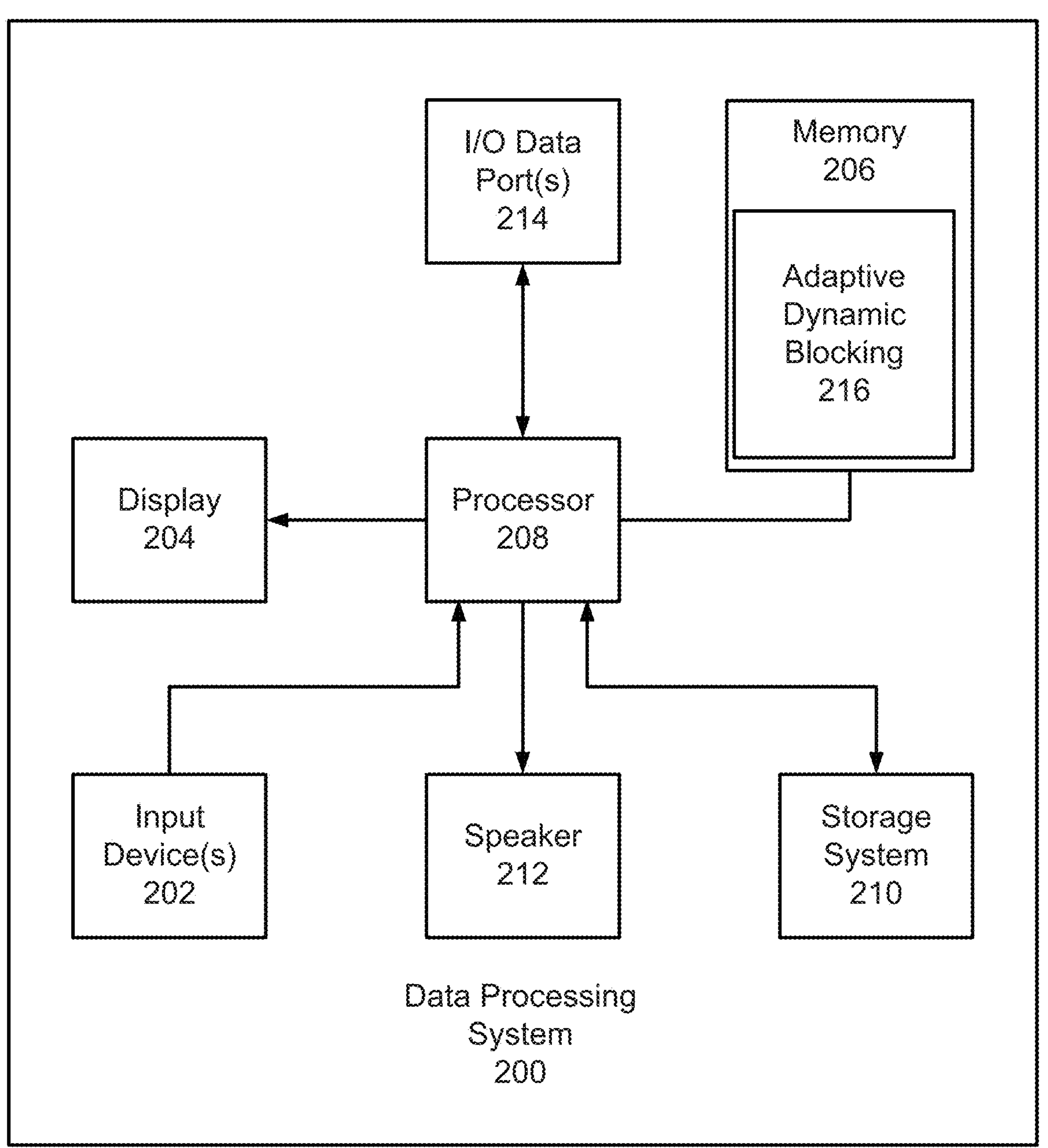
FIG. 2 illustrates a data processing system that may be used to implement the database management server host system of FIG. 1 in accordance with some embodiments of the inventive concept.

Referring now to FIG. 2, a data processing system 200 that may be used to implement the implement the database management server host system 115 of FIG. 1, in accordance with some embodiments of the inventive concept, comprises input device(s) 202, such as a keyboard or keypad, a display 204, and a memory 206 that communicate with a processor 208. The data processing system 200 may further include a storage system 210, a speaker 212, and an input/output (I/O) data port(s) 214 that also communicate with the processor 208. The storage system 210 may include removable and/or fixed media, such as floppy disks, ZIP drives, hard disks, or the like, as well as virtual storage, such as a RAMDISK. The I/O data port(s) 214 may be used to transfer information between the data processing system 200 and another computer system or a network (e.g., the Internet). These components may be conventional components, such as those used in many conventional computing devices, and their functionality, with respect to conventional operations, is generally known to those skilled in the art. The memory 206 may be configured with an adaptive dynamic blocking module 216 that may provide functionality that may include, but is not limited to, linking records in a database through dynamic control of maximum block sizes.

Figure 3:
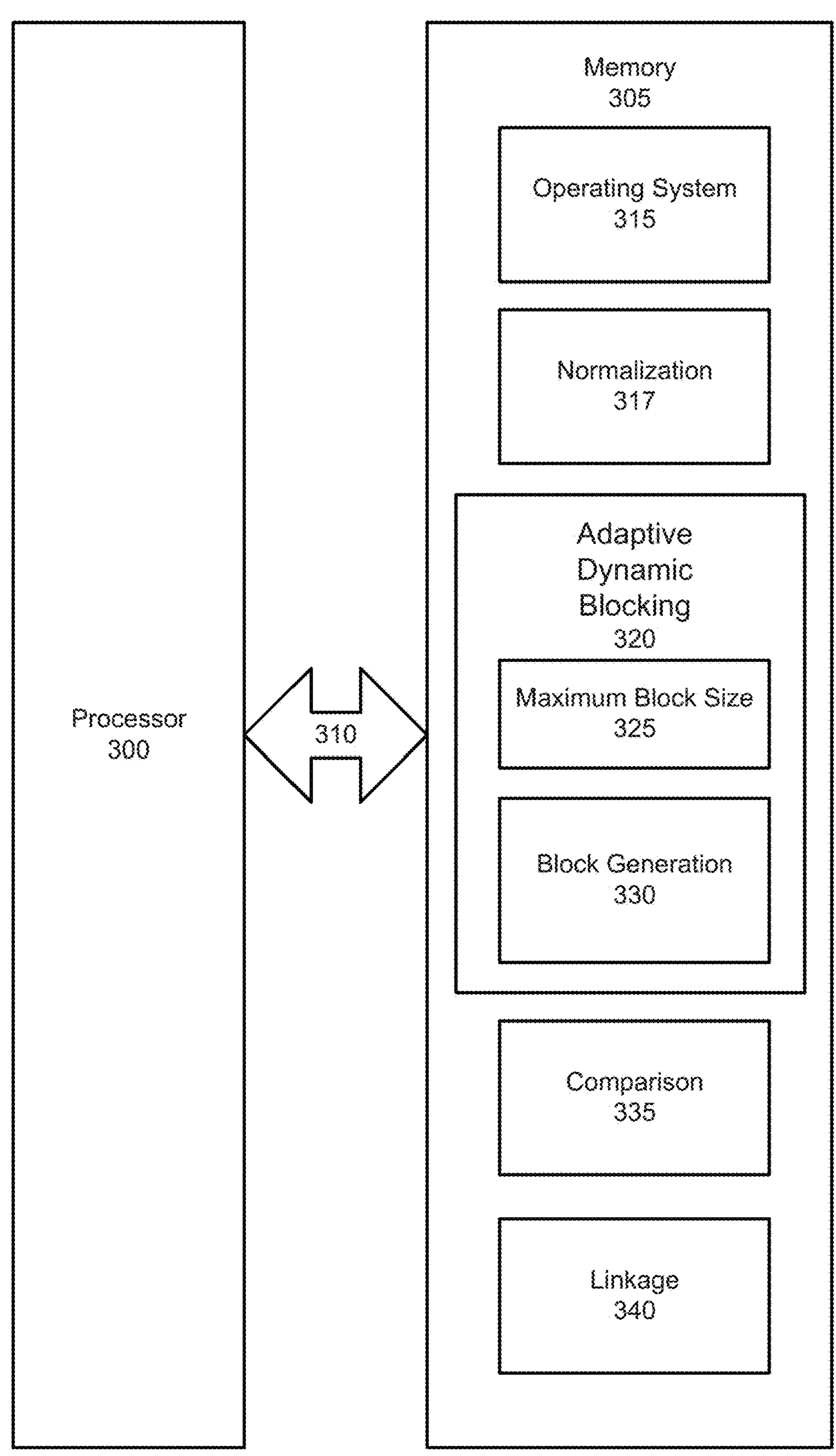
FIG. 3 is a block diagram that illustrates a software/hardware architecture for use in a database management server host system for linking records in a database using adaptive dynamic blocking in accordance with some embodiments of the inventive concept.

FIG. 3 illustrates a processor 300 and memory 305 that may be used in embodiments of data processing systems, such as the database management system server host 115 of FIG. 1 and the data processing system 200 of FIG. 2, respectively, for linking records in a database using adaptive dynamic blocking in accordance with some embodiments of the inventive concept. The processor 300 communicates with the memory 305 via an address/data bus 310. The processor 300 may be, for example, a commercially available or custom microprocessor. The memory 305 is representative of the one or more memory devices containing the software and data used for linking records in a database using adaptive dynamic blocking in accordance with some embodiments of the inventive concept. The memory 305 may include, but is not limited to, the following types of devices: cache, ROM, PROM, EPROM, EEPROM, flash, SRAM, and DRAM.

As shown in FIG. 3, the memory 305 may contain five or more categories of software and/or data: an operating system 315, a normalization module 317, an adaptive dynamic blocking module 320, a comparison module 335, and a linkage module 340. In particular, the operating system 315 may manage the data processing system's software and/or hardware resources and may coordinate execution of programs by the processor 300. Because the records in the database 125 may include datasets from different sources, the formats of various data items for the same attribute may differ. Thus, the normalization module 317 may be configured to normalize or pre-process the records to ensure that data values for the various fields are expressed in a consistent manner. The adaptive dynamic blocking module 320 may include a maximum block size module 325 and a block generation module 330. The maximum block size module 325 may be configured to generate, at run time, a plurality of maximum block sizes based on a plurality of blocking keys. The block generation module 330 may be configured to generate, at run time, the blocks based on the maximum block sizes. The comparison module 335 may be configured to perform comparisons between records in the blocks to determine similarities therebetween. The linkage module 340 may be configured to link those records in a block that are sufficiently similar to each other, e.g., satisfy a similarity threshold.

Although FIG. 3 illustrates hardware/software architectures that may be used in data processing systems, such as the database management system server host 115 of FIG. 1 and the data processing system 200 of FIG. 2, respectively, for linking records in a database using adaptive dynamic blocking in accordance with some embodiments of the inventive concept, it will be understood that embodiments of the present invention are not limited to such a configuration but is intended to encompass any configuration capable of carrying out operations described herein.

Computer program code for carrying out operations of data processing systems discussed above with respect to FIGS. 1-3 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the client devices or terminals 102, 105, 110, application server 112, and database management system server host 115 of FIG. 1, the data processing system 200 of FIG. 2, and the hardware/software architecture of FIG. 3, may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus of FIGS. 1-3 may be used to link records in a database using adaptive dynamic blocking according to various embodiments described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 206 coupled to the processor 208 and the memory 305 coupled to the processor 300 include computer readable program code that, when executed by the respective processors, causes the respective processors to perform operations including one or more of the operations described herein with respect to FIGS. 4-7.

Figure 4:
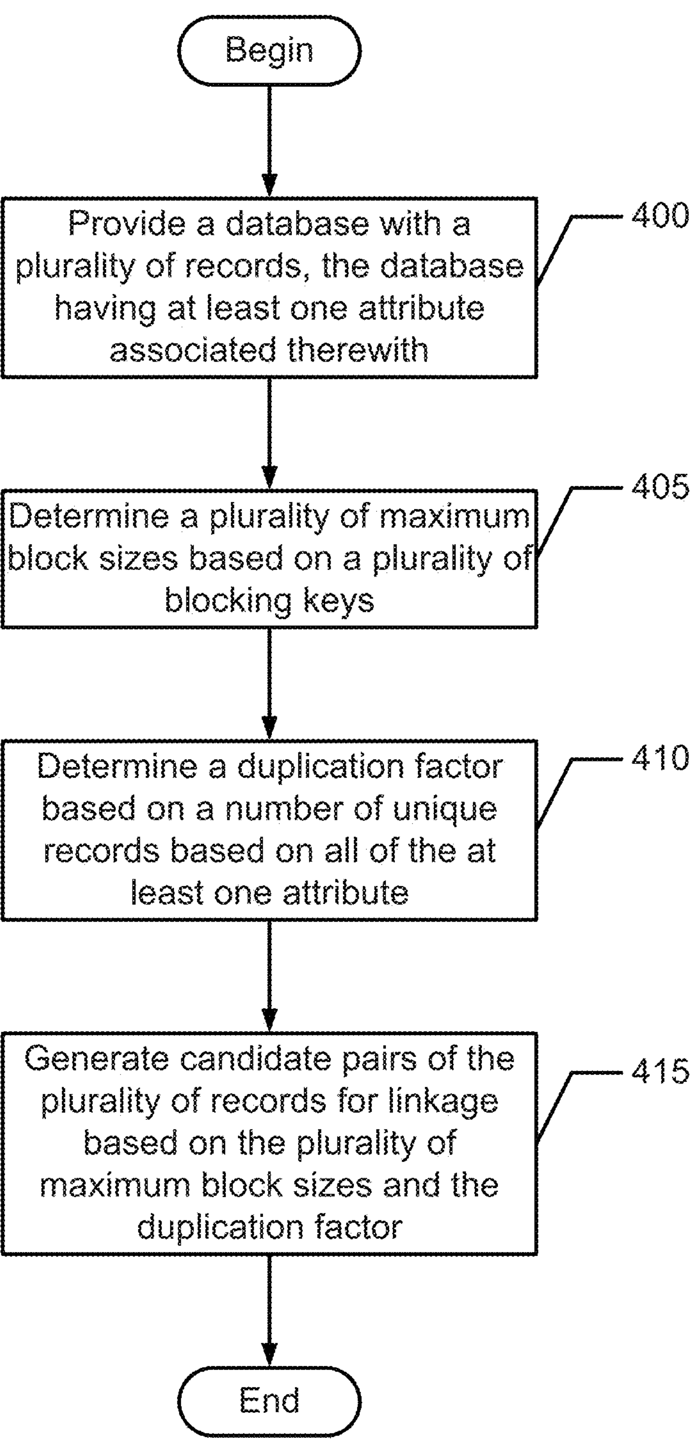
FIGS. 4-7 are flowchart diagrams that illustrate operations for linking records in a database using adaptive dynamic blocking in accordance with some embodiments of the inventive concept.

FIGS. 4-7 are flowchart diagrams that illustrate operations for linking records in a database using adaptive dynamic blocking in accordance with some embodiments of the inventive concept. Referring now to FIG. 4, operations begin at block 400 where a database 125 is provided that has at least one attribute associated therewith. A plurality of maximum block sizes is determined at block 405, which is a plurality of ideal maximum numbers of records in a plurality of blocks, respectively, based on a plurality of blocking keys. For example, if the database 125 has a set of attributes A1, A2, A3, . . . , An, and A1 is chosen as a blocking key, then those records having the same value in their field corresponding to attribute A1 may be grouped together in respective blocks K1, K2, K3, . . . having sizes C1, C2, C3, . . . . The maximum block size M may be given by the following equation:

$$M = \left(\text{Max}\,(C1,\,C2,\,\ldots\,)/\text{Average}\,(C1,\,C2,\,\ldots\,)\right) + \text{Average}\,(C1,\,C2,\,\ldots\,,) + \textit{Skewness}\,(C1,\,C2,\,\ldots\,).$$

Moreover, the maximum block sizes may be determined for a plurality of different blocking keys. For example, the maximum block size may be determined based on blocking keys as follows:

A1

A1, A2

A1, A2, . . . , An

That is, according to some embodiments of the inventive concept, blocking keys may be generated iteratively by adding an additional attribute to a previously generated key until the final blocking key corresponds to all the attributes.

The maximum block size M may be determined for each of these blocking keys and used for generating blocks for use in the comparing and linking operations as will be described herein according to some embodiments of the inventive concept.

Returning to FIG. 4, operations continue at block 410 where a duplication factor is determined based on a number of unique records of the plurality of records based on all of the at least one attribute, i.e., a blocking key generated to include all attributes of the database. The duplication factor may be given as 1−(the number of unique records/a total number of the plurality of records) according to some embodiments of the inventive concept. Candidate pairs of the plurality of records may be generated for linkage based on the plurality of maximum block sizes and the duplication factor ay block 415.

Figure 5:
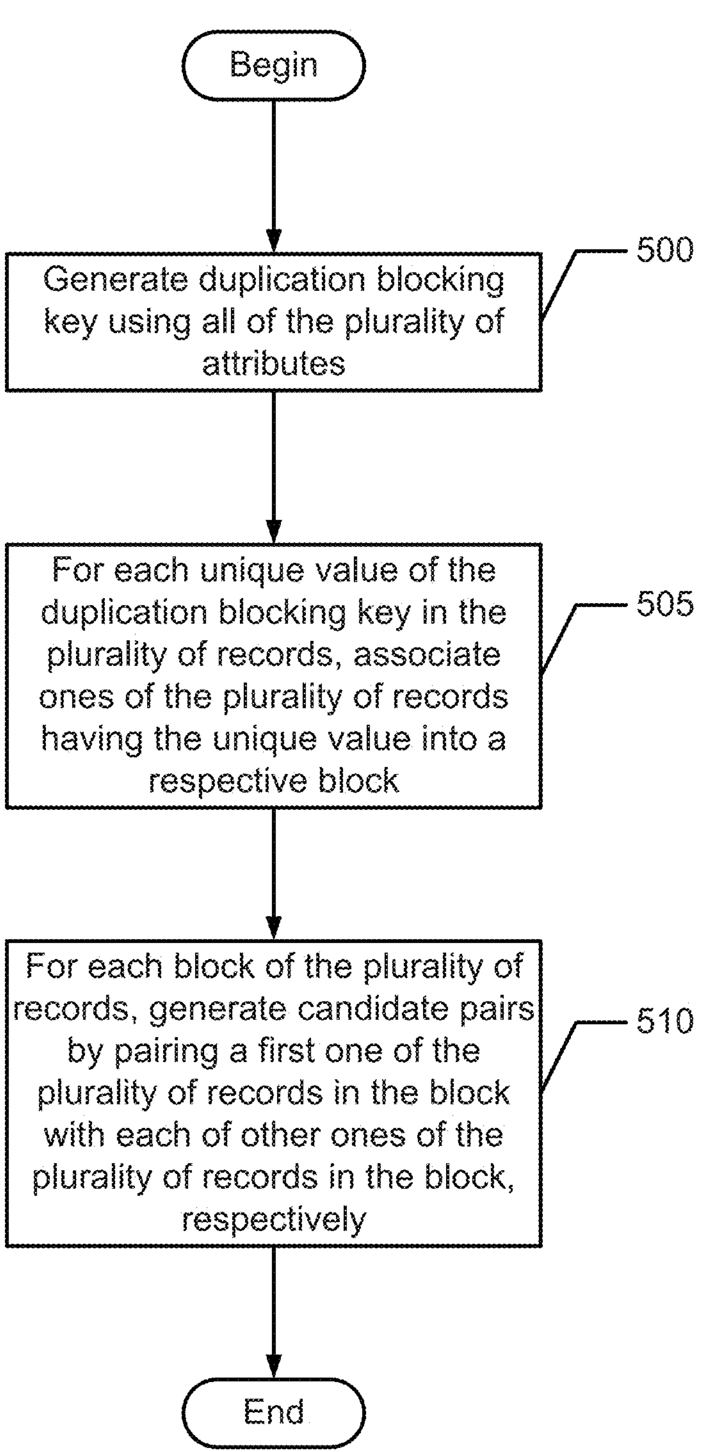

Referring now to FIG. 5, when the duplication factor is greater than a threshold, i.e., there are numerous duplicate records from the various datasets in the database 125, then operations begin at block 500 where a duplication blocking key is generated using all of the plurality of attributes. For each unique value of the blocking key in the plurality of records, ones of the plurality of records having the same unique value are grouped into the same respective block at block 505. For each block of the plurality of records, candidate pairs for linkage are generated by pairing a first one of the plurality of records with each of the other ones of the plurality of records in the block. That is, if the number of records in a block is numbered 1, 2, 3, . . . n, then the candidate pairs are generated as (1, 2), (1, 3), (1, 4), . . . (1, n).

Figure 6:
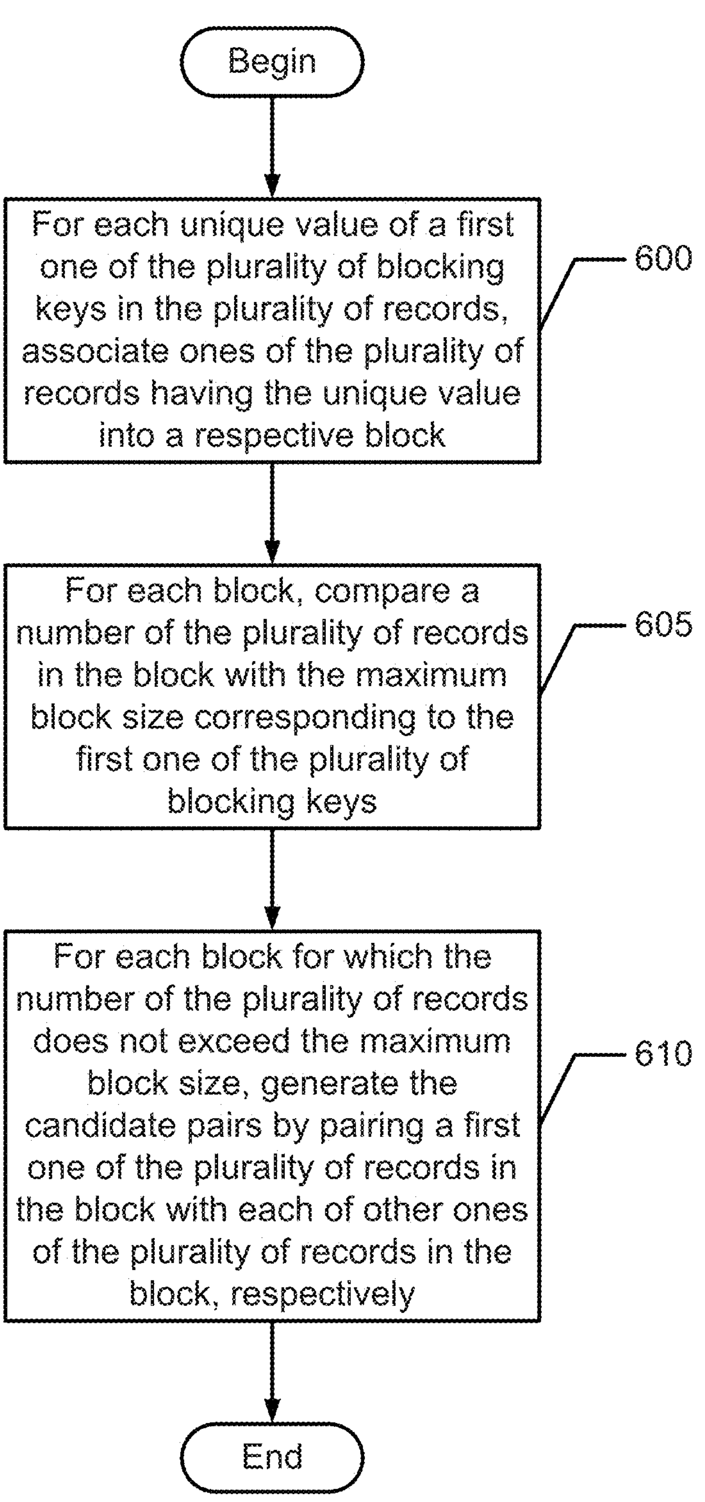

Referring now to FIG. 6, when the duplication factor is not greater than a threshold, then operations begin at block 600 where for each unique value of a first one of the plurality of blocking keys in the plurality of records, ones of the plurality of records having the unique value are grouped into a respective block. For each block, the number of records in the block is compared with the maximum block size corresponding to the first one of the plurality of blocking keys, e.g., (A1) at block 605. For each block for which the number of records does not exceed the maximum block size (e.g., acceptable blocks), the candidate pairs are generated by pairing a first one of the plurality of records in the block with each of the other ones of the plurality of records in the block, respectively at block 610. For example, if there are three blocks in which the number of records therein does not exceed the maximum block size, then the candidate pairs for linkage may be generated as follows:

Block 1 {record 1, record 3, record 10}

Block 2 {record 5, record 7, record 11}

Block 3 {record 2, record 4, record 12}

Candidate pairs: (1, 3), (1, 10), (5, 7), (5, 11), (2, 4), (2, 12)

According to some embodiment of the inventive concept, the candidate pairs generated from the various blocks need not be exhaustive, i.e., a candidate pair need not be generated for every possible combination of record pairs within a block. Instead, the candidate pairs in which the first record paired with each of the other records in the block may form a component or connected component, which may be viewed as a connected subgraph, which is not part of a larger connected subgraph. This component or connected component may be used at the linkage stage to determine which records to link to one another directly or indirectly.

Figure 7:
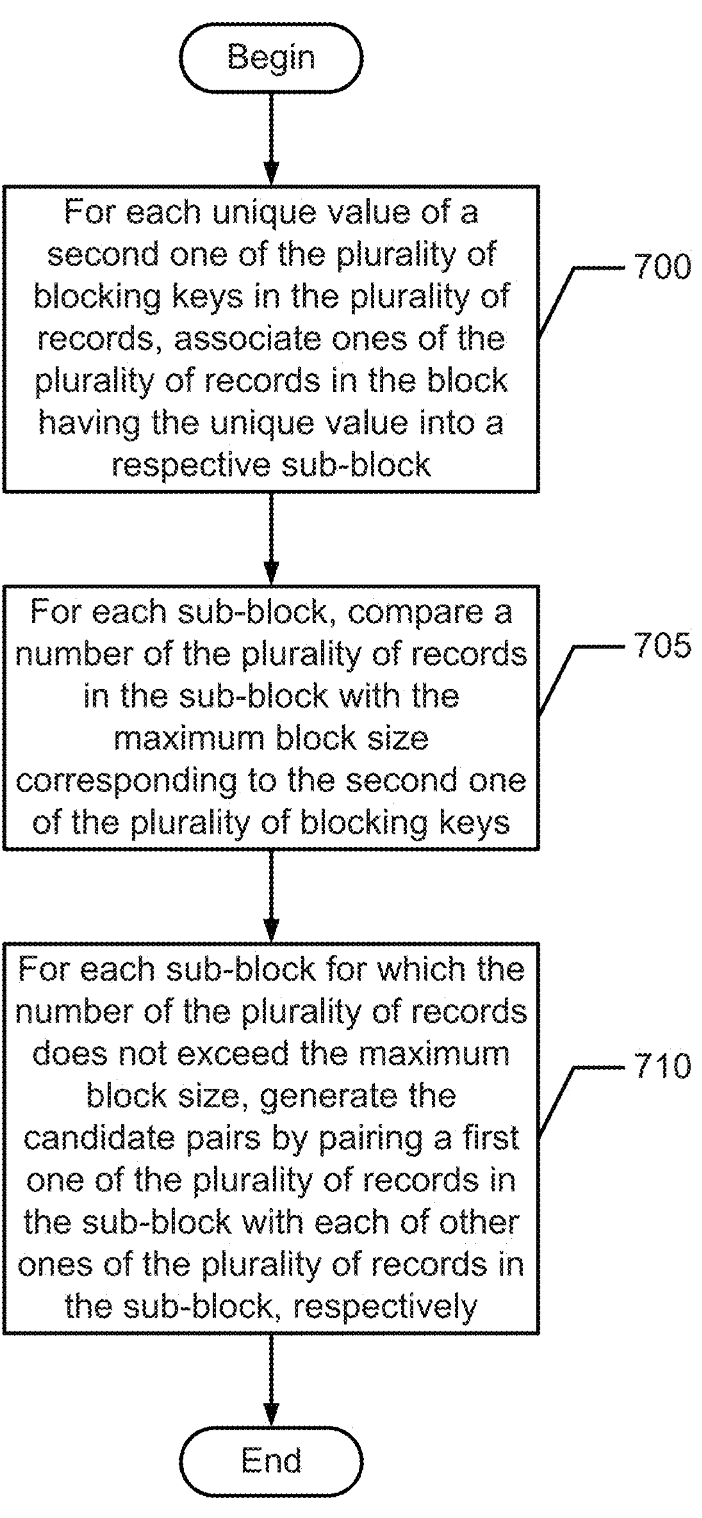

Referring now to FIG. 7, for those blocks at operation 605 of FIG. 6 that are determined to have a size greater than the maximum block size corresponding to the first one of the plurality of blocking keys (e.g., oversize blocks), then operations begin at block 700 where for each unique value of a second one of the plurality of blocking keys in the plurality of records, ones of the plurality of records in the block (e.g., oversize block) having the unique value are grouped into a respective sub-block. For example, the first one of the plurality of blocking keys may be based on attribute A1 and the second one of the plurality of blocking keys may be based on (A1, A2). For each sub-block, the number of records in the sub-block is compared with the maximum block size corresponding to the second one of the plurality of blocking keys at block 705. For each sub-block for which the number of records does not exceed the maximum block size (e.g., acceptable blocks), the candidate pairs are generated by pairing a first one of the plurality of records in the sub-block with each of the other ones of the plurality of records in the subblock, respectively at block 710 in the same manner as described above with respect to block 610 of FIG. 6.

The operations of FIG. 7 can be repeated for each oversize sub-block to create additional sub-blocks based on keys with more attributes, e.g., (A1), (A1, A2, A3); (A1, A2, A3, A4); . . . , (A1, A2, A3, A4, . . . , An). The process continues until there are no oversize sub-blocks or all of the attributes are exhausted. If all of the attributes are exhausted and there are one or more oversize sub-blocks remaining, then the records in these oversize sub-blocks may be added to the acceptable blocks for generating candidate pairs.

Some embodiments of the inventive concept may provide an adaptive dynamic blocking technique that can be used at run time to generate blocks that can be used for record comparison to identify candidate pairs for linkage. By determining maximum block sizes based on the blocking key used, the number of record comparisons can be reduced thereby reducing computing and/or memory resources. Moreover, the maximum block size may be determined at run time allowing for the dynamic determination of the resources needed for the record linkage operations. To reduce false negatives, the number of attributes used for a blocking key may be increased, which may allow a record to appear in multiple blocks.

FURTHER DEFINITIONS AND EMBODIMENTS

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A method comprising:

providing, by one or more processors, a database including a plurality of records, the database having a plurality of attributes associated therewith;

determining, by the one or more processors, a plurality of maximum block sizes as a plurality of ideal maximum numbers of the plurality of records in a plurality of blocks, respectively, based on a plurality of blocking keys;

determining, by the one or more processors and using a duplication blocking key that includes all of the plurality of attributes, a number of unique records of the plurality of records;

determining, by the one or more processors, a duplication factor based on the number of unique records and a total number of the plurality of records; and generating, by the one or more processors, candidate pairs of the plurality of records for linkage based on the plurality of maximum block sizes and the duplication factor, wherein generating the candidate pairs comprises:

determining the duplication factor is greater than a threshold;

for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

2. The method of claim 1, wherein a number of the plurality of attributes is N; and wherein the method further comprises:

generating, by the one or more processors, the plurality of blocking keys at least in part by:

generating a first one of the plurality of blocking keys by selecting a first one of the plurality of attributes as the first one of the plurality of blocking keys; then iteratively generating N−1 additional ones of the plurality of blocking keys by adding an additional one of the plurality of attributes to a previously created one of the plurality of blocking keys.

3. The method of claim 2, wherein determining the duplication factor comprises:

determining the duplication factor as 1−(the number of unique records/the total number of the plurality of records).

4. The method of claim 1, wherein determining the plurality of maximum block sizes comprises:

for each of the plurality of blocking keys performing operations comprising:

for each unique value of the respective one of the plurality of blocking keys, determining a number of ones of the plurality of records having the unique value, which is given by C1, C2, . . . ; and determining a respective maximum block size M for the respective one of the plurality of blocking keys as a function of at least Max (C1, C2, . . . ) and Average (C1, C2, . . . ).

5. The method of claim 4, wherein determining the respective maximum block size M for the respective one of the plurality of blocking keys includes determining M as:

$$M = (\text{Max}(C1, C2, \ldots)/\text{Average}(C1, C2, \ldots)) + \text{Average}(C1, C2, \ldots,) + \mathit{Skewness}(C1, C2, \ldots).$$

6. The method of claim 1, wherein the plurality of records comprises health care records associated with a patient.

7. The method of claim 1, wherein determining the duplication factor comprises determining the duplication factor based on the number of unique records divided by the total number of the plurality of records.

8. A system, comprising:

one or more processors; and one or more memories storing processor-executable instructions that, when executed by the one or more processors, cause the one or more processors to perform operations comprising:

providing a database including a plurality of records, the database having a plurality of attributes associated therewith;

determining a plurality of maximum block sizes as a plurality of ideal maximum numbers of the plurality of records in a plurality of blocks, respectively, based on a plurality of blocking keys;

determining, using a duplication blocking key that includes all of the plurality of attributes, a number of unique records of the plurality of records;

determining a duplication factor based on the number of unique records and a total number of the plurality of records; and generating candidate pairs of the plurality of records for linkage based on the plurality of maximum block sizes and the duplication factor, wherein generating the candidate pairs comprises:

determining the duplication factor is greater than a threshold;

for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

9. The system of claim 8, wherein a number of the plurality of attributes is N; and wherein the operations further comprise:

generating the plurality of blocking keys comprising:

generating a first one of the plurality of blocking keys by selecting a first one of the plurality of attributes as the first one of the plurality of blocking keys; then iteratively generating N−1 additional ones of the plurality of blocking keys by adding an additional one of the plurality of attributes to a previously created one of the plurality of blocking keys.

10. The system of claim 8, wherein determining the plurality of maximum block sizes comprises:

for each of the plurality of blocking keys performing operations comprising:

for each unique value of the respective one of the plurality of blocking keys, determining a number of ones of the plurality of records having the unique value, which is given by C1, C2, . . . ; and determining a respective maximum block size M for the respective one of the plurality of blocking keys as a function of at least Max (C1, C2, . . . ) and Average (C1, C2, . . . ).

11. The system of claim 10, wherein determining the respective maximum block size M for the respective one of the plurality of blocking keys includes determining M as:

$$M = (\text{Max}(C1, C2, \ldots)/\text{Average}(C1, C2, \ldots)) + \text{Average}(C1, C2, \ldots,) + \mathit{Skewness}(C1, C2, \ldots).$$

12. The system of claim 8, wherein the plurality of records comprises health care records associated with a patient.

13. The system of claim 8, wherein determining the duplication factor comprises determining the duplication factor based on the number of unique records divided by the total number of the plurality of records.

14. The system of claim 13, wherein determining the duplication factor comprises:

determining the duplication factor as 1−(the number of unique records/the total number of the plurality of records).

15. One or more non-transitory computer readable media storing processor-executable instructions that, when executed by one or more processors, cause the one or more processors to perform operations comprising:

providing a database including a plurality of records, the database having a plurality of attributes associated therewith;

determining a plurality of maximum block sizes as a plurality of ideal maximum numbers of the plurality of records in a plurality of blocks, respectively, based on a plurality of blocking keys;

determining, using a duplication blocking key that includes all of the plurality of attributes, a number of unique records of the plurality of records;

determining a duplication factor based on the number of unique records and a total number of the plurality of records; and generating candidate pairs of the plurality of records for linkage based on the plurality of maximum block sizes and the duplication factor, wherein generating the candidate pairs comprises:

determining the duplication factor is greater than a threshold;

for each unique value of the duplication blocking key in the plurality of records, associating ones of the plurality of records having the unique value into a respective block; and for each block of the plurality of records, generating the candidate pairs by pairing a first one of the plurality of records in the block with each of other ones of the plurality of records in the block, respectively.

16. The one or more non-transitory computer readable media of claim 15, wherein:

a number of the plurality of attributes is N; and the operations further comprise generating the plurality of blocking keys at least in part by:

generating a first one of the plurality of blocking keys by selecting a first one of the plurality of attributes as the first one of the plurality of blocking keys; then iteratively generating N−1 additional ones of the plurality of blocking keys by adding an additional one of the plurality of attributes to a previously created one of the plurality of blocking keys.

17. The one or more non-transitory computer readable media of claim 15, wherein determining the plurality of maximum block sizes comprises:

for each of the plurality of blocking keys performing operations comprising:

for each unique value of the respective one of the plurality of blocking keys, determining a number of ones of the plurality of records having the unique value, which is given by C1, C2, . . . ; and determining a respective maximum block size M for the respective one of the plurality of blocking keys as a function of at least Max (C1, C2, . . . ) and Average (C1, C2, . . . ).

18. The one or more non-transitory computer readable media of claim 15, wherein the plurality of records comprises health care records associated with a patient.

19. The one or more non-transitory computer readable media of claim 15, wherein determining the duplication factor comprises determining the duplication factor based on the number of unique records divided by the total number of the plurality of records.

20. The one or more non-transitory computer readable media of claim 19, wherein determining the duplication factor comprises:

determining the duplication factor as 1−(the number of unique records/the total number of the plurality of records).

* * * * *